United States Patent
De Carvalho et al.

(10) Patent No.: US 11,324,588 B2
(45) Date of Patent: May 10, 2022

(54) DIFFRACTIVE INTRAOCULAR LENS

(71) Applicant: Mediphacos Industrias Medicas S/A, Belo Horizonte (BR)

(72) Inventors: Luiz Melk De Carvalho, Belo Horizonte (BR); Lucas Campos Silva, Belo Horizonte (BR); Otavio Gomes De Oliveira, Belo Horizonte (BR)

(73) Assignee: Mediphacos Industrias Medicas S/A, Belo Horizonte (BR)

( * ) Notice: Subject to any disclaimer, the term of this patent is extended or adjusted under 35 U.S.C. 154(b) by 2 days.

(21) Appl. No.: 16/365,800

(22) Filed: Mar. 27, 2019

(65) Prior Publication Data

US 2019/0307557 A1 Oct. 10, 2019

Related U.S. Application Data

(60) Provisional application No. 62/654,639, filed on Apr. 9, 2018.

(51) Int. Cl.
*A61F 2/16* (2006.01)

(52) U.S. Cl.
CPC .......... *A61F 2/1654* (2013.01); *A61F 2/1627* (2013.01)

(58) Field of Classification Search
CPC ............ G02B 27/4205; G02B 27/4233; A61F 2/1654; A61F 2/1627; A61F 2/1648
See application file for complete search history.

(56) References Cited

U.S. PATENT DOCUMENTS

| | | | |
|---|---|---|---|
| 2011/0270390 A1 | 11/2011 | Kobayashi et al. | 623/6.38 |
| 2011/0292335 A1 | 12/2011 | Schwiegerling et al. | 651/161 |
| 2012/0224138 A1* | 9/2012 | Cohen | A61F 2/1618 351/159.11 |
| 2012/0283825 A1 | 11/2012 | Houbrechts et al. | 623/6.27 |
| 2014/0172088 A1 | 6/2014 | Carson et al. | 623/6.3 |
| 2017/0071727 A1* | 3/2017 | Hyde | A61B 5/0031 |
| 2017/0252151 A1 | 9/2017 | Mackool | |
| 2019/0142577 A1* | 5/2019 | Xie | A61F 2/1618 623/6.28 |
| 2020/0310159 A1 | 10/2020 | Zhang | |

FOREIGN PATENT DOCUMENTS

| | | |
|---|---|---|
| EP | 2 377 493 A1 | 10/2011 |
| EP | 3 435 143 A1 | 1/2019 |
| WO | WO-94/11765 A1 | 5/1994 |

(Continued)

OTHER PUBLICATIONS

Ming, Arthur Lim Siew, et al., "Color Atlas of Opthamology", World Science, 1995, 165 pgs.

(Continued)

*Primary Examiner* — Jerrah Edwards
*Assistant Examiner* — Aren Patel
(74) *Attorney, Agent, or Firm* — Harrington & Smith

(57) ABSTRACT

The present invention refers to an intraocular lens provided with specific diffractive profile, in which each step height is individually defined, with no fixed pattern. The intraocular lens provides a better control of the luminous efficiency of each focal point, guaranteeing more flexibility and customization, being adaptable to the optical quality that the patient needs.

21 Claims, 4 Drawing Sheets

(56) References Cited

FOREIGN PATENT DOCUMENTS

| WO | WO-2007/092949 A1 | 8/2007 |
| WO | WO-2020/132703 A1 | 6/2020 |

OTHER PUBLICATIONS

O'Shea, Donald C., et al., "Diffractive Optics, Design, Fabrication, and Test", © 2004, The society of Photo-Optical Instrumentation Engineers, 253 pgs.

Davison, James A., "Deciphering Diffraction, How the Restor's apodized, refractive, diffractive optic works", Jun. 2005, Cataract & Refractive Surgery Today, 5 pgs.

Schwiegerling, Jim, "Diffraction efficiency and aberrations of diffractive elements obtained from orthogonal expansion of the point spread function", © 2016 SPIE, 8 pgs.

Gatinel, Damien, et al., "Design and qualification of diffractive trifocal optical profile for intraocular lenses", © 2011 ASCRS and ESCRS, 8 pgs.

J. A. Davison and M.J. Simpson, "History and Development of the Apodized Diffractive Intraocular Lens", J Cataract Refract Surg, pp. 849-858, 2006.

Lenkova, G.A., "Methods for Investigating Optical Characteristics of Bifocal Diffractive-Refractive Intraocular Lenses", *Optoelectronics, Instrumentation and Data Processing*, 2007, vol. 43, No. 3, pp. 262-273.

\* cited by examiner

DIFFRACTIVE INTRAOCULAR LENS

CROSS REFERENCE TO RELATED APPLICATION

This patent application is a U.S. utility application that claims priority to U.S. provisional application No. 62/654,639 filed Apr. 9, 2018 which is hereby incorporated by reference in its entirety.

FIELD OF THE INVENTION

The present invention belongs to the field of ophthalmologic implants and refers to an intraocular lens provided with specific diffractive profile.

BACKGROUND OF THE INVENTION

As it is known from the state of the art, intraocular lenses, commonly called IOLs are medical devices used for ocular implant in surgeries for cataract treatment. Generally, lenses are implanted for replacement of the crystalline lens, a natural human eye lens which, in case of suffering from cataract, will become opaque and as a result the passage of light to the retina will not occur, thus compromising the eyesight.

The intraocular lens is an artificial lens that presents itself as a very effective solution in the treatment of cataracts (Ming & Constable, 1995). Its structure is composed of an optic region and haptic structures, which are responsible for stabilizing the lens in the eye (FIG. 1).

The optical region of an IOL is formed by refractive and/or diffractive convex surfaces. A diffractive multifocal intraocular lens (MIOL) is formed by a profile of steps that causes the incident beam of light to undergo diffraction. In this way the incident beam is decomposed into several secondary beams (called diffractive orders) whose amount of light energy corresponds to a percentage of the incident light energy. Through this phenomenon, the diffractive orders with the highest percentage of light energy will be responsible for the formation of multiple focal points. The factors that will determine the energy distribution of diffractive orders are the height of the step and the wavelength of the light in propagation, that is, for a given wavelength of light it is possible to control the percentage of light energy transmitted in each diffractive order through the height of the diffractive step of the IOL. FIG. 2 illustrates the working principle of a diffractive MIOL. The incident beam will be diffracted in each of its steps and according to the height of the MIOL steps only in some diffractive orders (order 0, +1 and +2 are highlighted, and will be responsible for the formation of the main focal points on the optical axis (O'Shea, Suleski, Kathman, & Prather, 2004).

One of the most basic designs of diffractive multifocal IOL present on the market is formed by a set of diffractive steps with constant height on one side of the optical region of the lens (FIG. 3). This configuration allows two diffractive orders to be prioritized, guaranteeing the creation of two focal points in the image plane (bifocal lens). Other diffractive orders still contribute part of the incident energy, but are insignificant in relation to the two major orders for creating useful focal points for vision. In such a design it is common to prioritize the orders 0 and +1, which are responsible, respectively, for the formation of the far focus and the near focus. The amount of energy that is transmitted for each diffractive order, i.e. for each focus, depends on the height of the step of the profile (of the order of µm). In general, a step height is chosen that allows a division of light energy for the orders 0 and +1 in the same ratio, that is, 41% of the total incident energy is directed to the order 0, 41% of the total incident energy is directed to order 1 and the remainder to the other orders.

Considering the step height of the diffractive profile that guarantees a distribution of equal light energy between the 0 and +1 orders, it is noticed that a decrease in the height of the grid steps causes the distant focus to be prioritized (have a higher percentage of energy) in relation to the near focus. In this sense, there are lenses in the market that show a decrease in the height of the step as one moves towards the end of the optical area. Such an approach causes the distant focus to receive a higher percentage of light energy as the pupil increases. The decreasing of the heights of the steps is called apodization (FIG. 4) (Davison, 2005).

The MIOLs presented so far are bifocal lenses, however, there are already on the market LIOMs that allow the creation of 3 focal points useful to the vision (trifocal MIOLs). One of the lenses that allows such behavior presents diffractive steps with two different heights alternating between them (FIG. 5) (Schwiegerling, 2016).

Another PhysiOL lens consists of adding two apodized diffractive networks (FIG. 6), resulting in a diffractive structure with alternately and gradually smaller steps (FIG. 7) (Gatinel, Pagnoulle, Houbrechts, & Gobin, 2011). Such structure is better described on patent application US 2011/0270390.

Finally, other intraocular lenses are described in the state of the art, which comprise diffractive "zones" which present different diffractive profiles among them. Nevertheless, within each zone, it can be seen a fixed diffractive profile, such as a constant step height, or an apodized profile. Examples of such intraocular lenses can be found on patent applications US 2017/0252151, US 2014/0172088 and US 2012/0224138.

As it possible to see, all intraocular lenses described above have a fixed pattern for defining the step heights of the diffractive profiles. Either the step heights are constant, or they vary according to a fixed pattern (constant decrease, alternate heights, alternate zones, etc.).

Therefore, there is still a need in the state of the art for the development of an intraocular lens in which each step height is individually defined and optimized for a better control of the luminous efficiency of each focal point.

Objectives of the Invention

Therefore, in view of the foregoing, one of the objectives of the present invention is to provide an intraocular lens with a specific diffractive profile, in which each step height is individually defined, with no fixed pattern.

More particularly, one of the objectives of the present invention is to provide an intraocular lens whose diffractive profile is able to provide a better control of the luminous efficiency of each focal point, guaranteeing more flexibility and customization to the intraocular lens which can adapt the optical quality to the patient needs. Such patient needs include, for instance, the requirement for better far vision for drivers under both photopic and scotopic conditions, and the requirements for better intermediate vision for those who work in offices.

SUMMARY OF THE INVENTION

The above-mentioned objectives of the present invention are achieved by means of an intraocular lens comprising: an anterior surface, a posterior surface, wherein on at least one of the anterior or posterior surfaces a diffractive profile is formed, said diffractive profile providing for at least two diffractive focal points, wherein said diffractive profile has a plurality of steps with corresponding steps heights, each step height being individually defined, the first step height being between 0.30 μm and 4.5 μm, each subsequent step height being defined as a percentage of the step height of the immediate previous step.

Preferably, the diffractive profile provides for three or four diffractive focal points. The diffractive profile can also provide for a focal region characterized as extended depth-of-focus.

In a particular advantageous embodiment, the second step height varies from 40 to 100% of the first step height; the third step height varies from 120 to 200% of the second step height; the fourth step height varies from 20 to 80% of the third step height; the fifth step height varies from 110 to 400% of the fourth step height; the sixth step height varies from 20 to 120% of the fifth step height; the seventh step height varies from 100 to 380% of the sixth step height; the eighth step height varies from 5 to 80% of the seventh step height; and the ninth step height varies from 190 to 660% of the eighth step height.

In another particular advantageous embodiment, the second step height varies from 220 to 280% of the first step height; the third step height varies from 20 to 80% of the second step height; the fourth step height varies from 220 to 280% of the third step height; the fifth step height varies from 5 to 80% of the fourth step height; the sixth step height varies from 140 to 590% of the fifth step height; the seventh step height varies from 20 to 90% of the sixth step height; the eighth step height varies from 90 to 250% of the seventh step height; and the ninth step height varies from 10 to 100% of the eighth step height.

Preferably, the number of steps of the diffractive profile varies from 4 to 43.

BRIEF DESCRIPTION OF THE DRAWINGS

The present invention will be described in detail through the figures below, wherein.

DETAILED DESCRIPTION OF THE INVENTION

In accordance with the schematic figures mentioned above, some examples of the possible embodiments of the present invention will be described in more details below but a in merely exemplificative and not limitative manner, since the object of the present invention can comprise different details and structural and dimensional aspects without however departing from the desired scope of protection.

Figure 1:
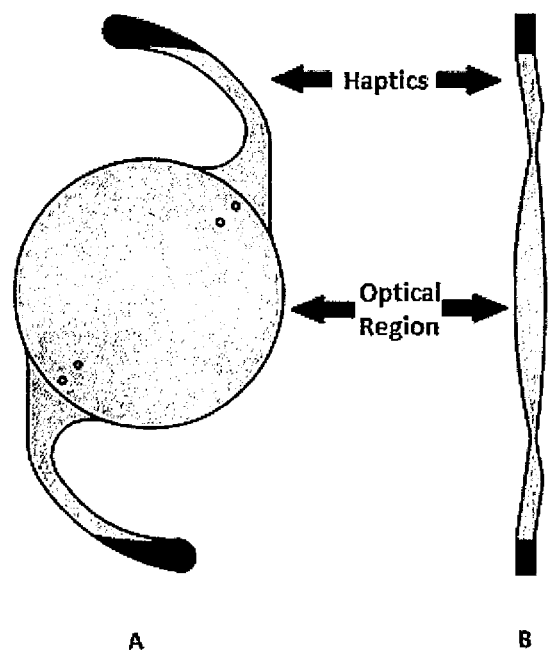
FIG. 1 is a generic representation of the basic components of an intraocular lens, in accordance with the state of the art.
Figure 2:
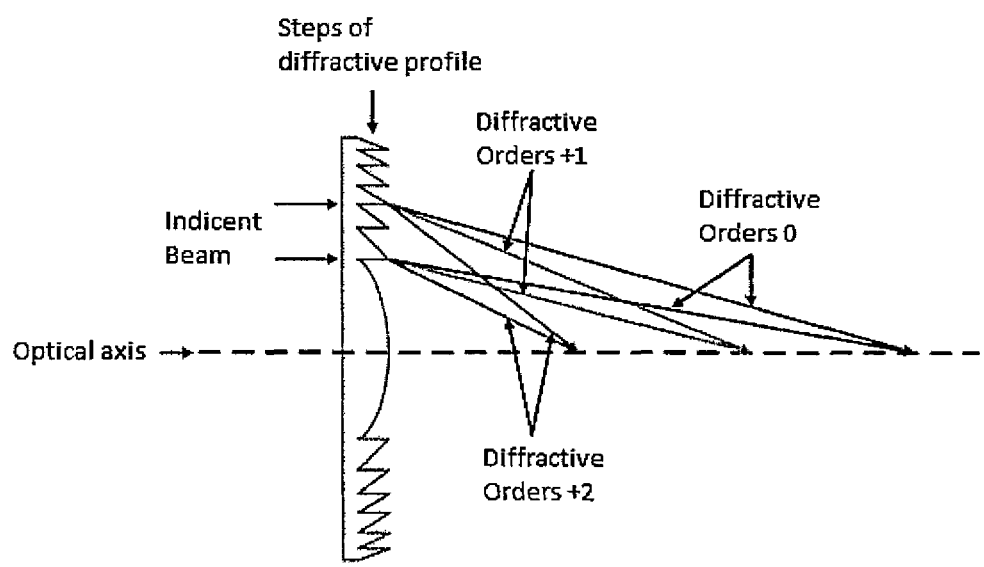
FIG. 2 is, a generic representation of the working principle of a diffractive intraocular lens, in accordance with the state of the art.
Figure 3:
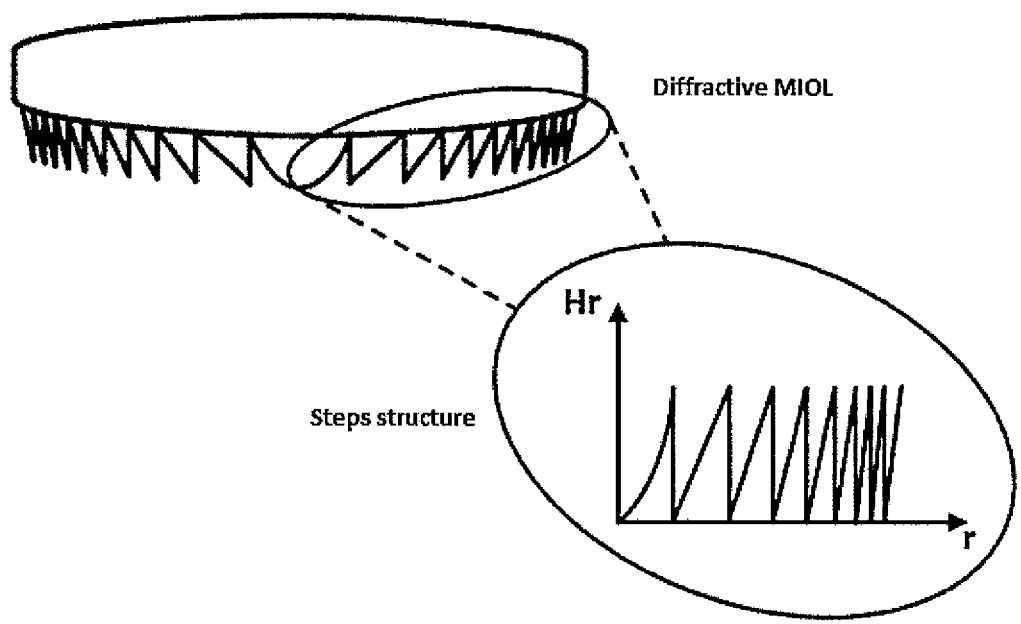
FIG. 3 is a representation of an intraocular lens of the state of the art, which diffractive steps have constant height.
Figure 4:
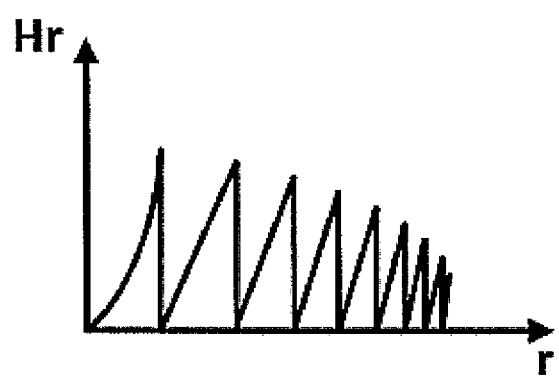
FIG. 4 is a representation of an intraocular lens of the state of the art, which diffractive steps are apodized, with decreasing step heights.
Figure 5:
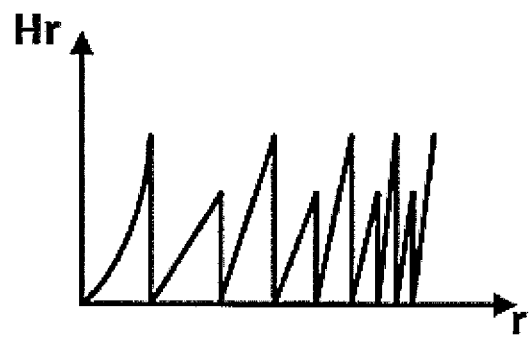
FIG. 5 is a representation of an intraocular lens of the state of the art, which diffractive steps have alternating step heights.
Figure 6:
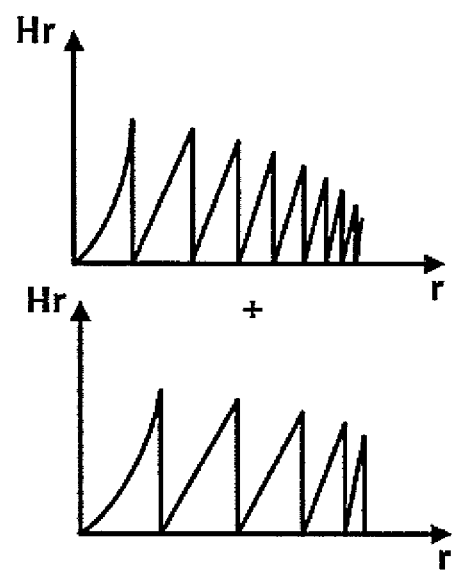
FIGS. 6 and 7 are a representation of an intraocular lens of the state of the art, which combine to apodized diffractive profiles, to create a diffractive structure with alternately and gradually smaller steps.
Figure 7:
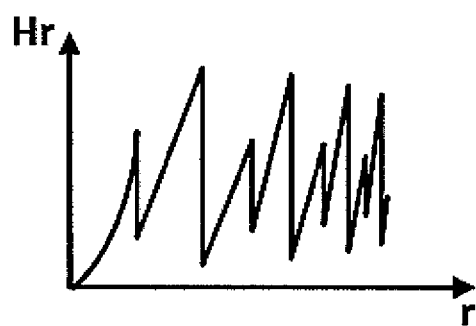
Figure 8:
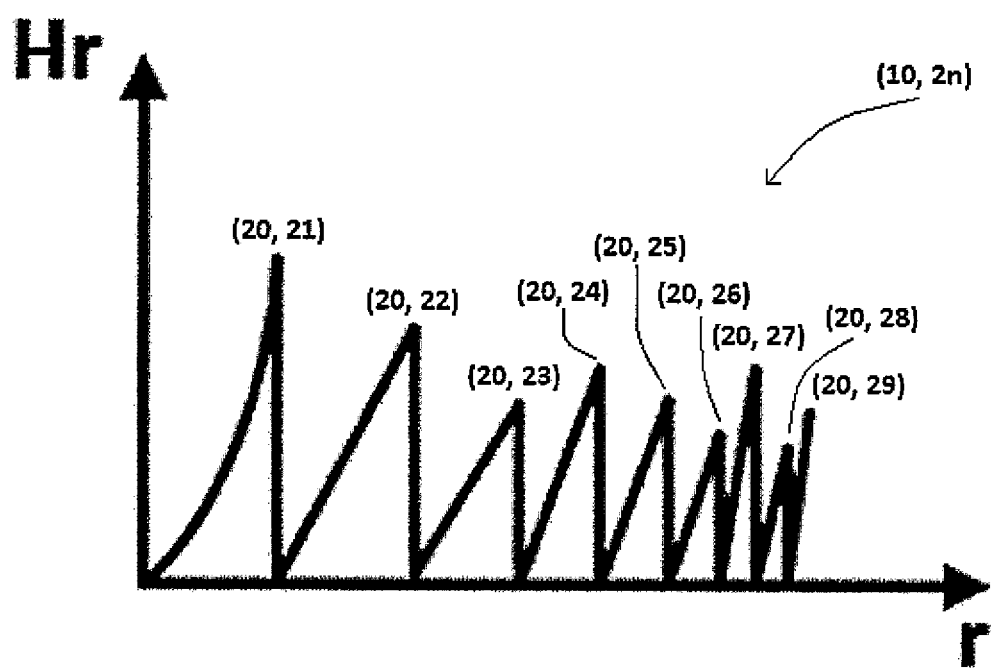
FIG. 8 is a representation of the intraocular lens in accordance with present invention, wherein each step height is individually defined.

Hence, the present invention refers to an intraocular lens based on a diffractive profile (10) in which each step (20, 2n) has been optimized individually. Such an approach causes each diffractive step (20, 2n) to have a different height without following an apodized pattern and without alternating the height of the steps (20, 2n) along the diffractive profile as shown in the prior art disclosed in FIGS. 1 to 7.

In other words, the distribution of heights of the steps (20, 2n) along the diffractive profile (10) is random, so that no pattern of alternation or apodization of the steps (20, 2n) is followed.

In view of this, the intraocular lens of the present invention comprises an anterior surface and a posterior surface. On at least one of the anterior or posterior surfaces, a diffractive profile (10) is formed.

Said diffractive profile (10) provides for at least two diffractive focal points, but preferably provide for three or four focal points. The diffractive profile (10) can also provide for a focal region characterized as extended depth-of-focus.

Said diffractive profile (10) has a plurality of steps (20, 2n) with corresponding steps heights, each step height being individually defined, without any pattern, either constant, or apodized/alternate.

The first step (20, 21) height, that is, the height of the step that is closer to the center of the anterior or posterior surface of the intraocular lens, is defined between 0.30 μm and 4.5 μm.

Each subsequent step height is defined as a percentage of the step height of the immediate previous step.

In other words, the height of the diffractive steps (20, 2n) is optimized individually, and there is an interdependence between pairs of steps starting from the first step (20, 21).

In this sense, the second step (20, 22) height is optimized within a range, which is a percentage of the height of the first step (20, 21); the third step (20, 23) is optimized within a range, which is a percentage of the height of the second step (20, 22) and so on.

In a particular advantageous embodiment, the second step (20, 22) height varies from 40 to 100% of the first step (20, 21) height; the third step (20, 23) height varies from 120 to 200% of the second step (20, 22) height; the fourth step (20, 24) height varies from 20 to 80% of the third step (20, 23) height; the fifth step (20, 25) height varies from 110 to 400% of the fourth step (20, 24) height; the sixth step (20, 26) height varies from 20 to 120% of the fifth step (20, 25) height; the seventh step (20, 27) height varies from 100 to 380% of the sixth step (20, 26) height; the eighth step (20, 28) height varies from 5 to 80% of the seventh step (20, 27) height; and the ninth step (20, 29) height varies from 190 to 660% of the eighth step (20, 28) height.

In another particular advantageous embodiment, the second step (20, 22) height varies from 220 to 280% of the first step (20, 21) height; the third step (20, 23) height varies from 20 to 80% of the second step (20, 22) height; the fourth step (20, 24) height varies from 220 to 280% of the third step (20, 23) height; the fifth step (20, 25) height varies from 5 to 80% of the fourth step (20, 24) height; the sixth step (20, 26) height varies from 140 to 590% of the fifth step (20, 25) height; the seventh step (20, 27) height varies from 20 to 90% of the sixth step (20, 26) height; the eighth step (20, 28) height varies from 90 to 250% of the seventh step (20, 27) height; and the ninth step (20, 29) height varies from 10 to 100% of the eighth step (20, 28) height.

Preferably, the total number (n) of steps (20, 2n) of the diffractive profile (10) varies from 4 to 43.

In relation to the structure of the intraocular lens itself, the anterior and posterior surfaces preferably present convex curvatures, one being refractive and the other diffractive or hybrid (diffractive part and refractive part).

Each of the surfaces may be spherical or aspherical. The diffractive profile (10) is able to create three foci based on the diffractive orders 0 (far focus), +1 (intermediate focus) and +2 (near focus), with additional between far and near focus, ranging from +1 D to +4 D.

The shape of the diffractive steps (20, 2n) preferably follows a kinoform pattern.

As defined above, the intraocular lens of the present invention is capable of creating 2 (bifocal), 3 (trifocal) or 4 (quadrifocal) focal points or generate a depth of focus.

EXAMPLES

Some examples of ranges of values for the step (20, 2n) heights of the diffractive profiles in accordance with present invention are presented below.

Example 1

Models M1-M6 refer to trifocal intraocular lens described on Table 1. The total number (n) of steps (20, 2n) presented may vary according to the additional defined for the diffractive profile.

In this example, the Step-2 refers to second step (20, 22), and its step height is defined as a percentage range from the first step (20, 21). Step-3 refers to the third step (20, 23), and its step height is defined as a percentage range from the second step (20, 22), and so on. In this particular example, the models M1-M6 comprise 17 steps.

TABLE 1 ranges of values for the step heights of the diffractive profiles (10) for 6 models of intraocular lens in accordance with present invention.

| Models | Step-2 | Step-3 | Step-4 | Step-5 | Step-6 | Step-7 | Step-8 | Step-9 |
|---|---|---|---|---|---|---|---|---|
| M1 | 40-80% | 150-200% | 20-60% | 110-400% | 20-100% | 300-380% | 10-60% | 300-360% |
| M2 | 40-100% | 120-190% | 20-80% | 110-180% | 40-120% | 160-230% | 10-50% | 280-340% |
| M3 | 40-80% | 150-200% | 20-60% | 110-400% | 20-100% | 160-230% | 10-60% | 590-640% |
| M4 | 40-100% | 120-190% | 20-80% | 110-180% | 40-120% | 100-150% | 20-80% | 190-240% |
| M5 | 40-80% | 150-200% | 20-60% | 110-400% | 20-100% | 320-380% | 5-30% | 590-660% |
| M6 | 40-100% | 120-190% | 20-80% | 110-180% | 40-120% | 120-180% | 20-80% | 220-280% |

| Models | Step-10 | Step-11 | Step-12 | Step-13 | Step-14 | Step-15 | Step-16 | Step-17 |
|---|---|---|---|---|---|---|---|---|
| M1 | 10-60% | 300-360% | 20-70% | 180-230% | 20-80% | 200-270% | 20-70% | 250-330% |
| M2 | 30-80% | 180-230% | 10-70% | 250-320% | 20-70% | 250-320% | 15-70% | 290-350% |
| M3 | 5-30% | 200-270% | 20-80% | 930-990% | 120-180% | 20-70% | 20-70% | 80-130% |
| M4 | 30-90% | 140-200% | 20-80% | 200-250% | 10-70% | 220-300% | 10-60% | 150-210% |
| M5 | 20-80% | 190-250% | 5-70% | 230-300% | 10-70% | 320-380% | 5-40% | 80-130% |
| M6 | 30-90% | 90-150% | 20-80% | 120-180% | 20-80% | 280-340% | 50-110% | 60-120% |

Example 2

Models M1-M3 refer to depth-of-focus intraocular lens described on Table 2. The total number (n) of steps (20, 2n) presented may vary according to the additional defined for the diffractive profile.

In this example, the Step-2 refers to second step (20, 22), and its step height is defined as a percentage range of the first step (20, 21). Step-3 refers to the third step (20, 23), and its step height is defined as a percentage range of the second step (20, 22), and so on. In this particular example, the models M1-M3 comprise 9 steps.

TABLE 2 ranges of values for the step heights of the diffractive profiles (10) for 3 models of intraocular lens in accordance with present invention.

| Models | Step-2 | Step-3 | Step-4 | Step-5 | Step-6 | Step-7 | Step-8 | Step-9 |
|---|---|---|---|---|---|---|---|---|
| M1 | 220-280% | 20-80% | 220-280% | 5-50% | 520-590% | 30-90% | 90-150% | 20-80% |
| M2 | 220-280% | 20-80% | 220-280% | 20-80% | 140-200% | 30-90% | 180-250% | 10-70% |
| M3 | 220-280% | 20-80% | 220-280% | 20-70% | 150-210% | 20-90% | 150-200% | 30-100% |

It is important to point out that the description above only intends to describe in an exemplificative manner all the preferred embodiments of the intraocular lens of the present invention. Hence, as understood by a person skilled in the art, the invention contemplates several construction modifications, variations and combinations of the features exerting the same function in substantially the same form to arrive at the same results, which are within the scope of protection limited by the appended claims.

The invention claimed is:

1. An intraocular lens comprising:
    an anterior surface,
    a posterior surface, and
    wherein on at least one of the anterior or posterior surfaces a diffractive profile is formed, said diffractive profile providing for at least two diffractive focal points and comprising a non-apodized kinoform diffractive profile with equal area,
    wherein said diffractive profile has a plurality of steps with corresponding steps heights, each step height being individually defined,
    the first step height being between 0.30 µm and 4.5 µm,
    each subsequent step height being defined as a percentage of the step height of the immediate previous step.

2. Intraocular lens, in accordance with claim 1, wherein the diffractive profile provides for three diffractive focal points.

3. Intraocular lens, in accordance with claim 1, wherein the diffractive profile provides for four diffractive focal points.

4. Intraocular lens, in accordance with claim 1, wherein the diffractive profile provides for a focal region characterized as extended depth-of-focus.

5. Intraocular lens, in accordance with claim 1, wherein the second step height varies from 40 to 100% of the first step height.

6. Intraocular lens, in accordance with claim 1, wherein the third step height varies from 120 to 200% of the second step height.

7. Intraocular lens, in accordance with claim 1, wherein the fourth step height varies from 20 to 80% of the third step height.

8. Intraocular lens, in accordance with claim 1, wherein the fifth step height varies from 110 to 400% of the fourth step height.

9. Intraocular lens, in accordance with claim 1, wherein the sixth step height varies from 20 to 120% of the fifth step height.

10. Intraocular lens, in accordance with claim 1, wherein the seventh step height varies from 100 to 380% of the sixth step height.

11. Intraocular lens, in accordance with claim 1, wherein the eighth step height varies from 5 to 80% of the seventh step height.

12. Intraocular lens, in accordance with claim 1, wherein the ninth step height varies from 190 to 660% of the eighth step height.

13. Intraocular lens, in accordance with claim 1, wherein the second step height varies from 220 to 280% of the first step height.

14. Intraocular lens, in accordance with claim 1, wherein the third step height varies from 20 to 80% of the second step height.

15. Intraocular lens, in accordance with claim 1, wherein the fourth step height varies from 220 to 280% of the third step height.

16. Intraocular lens, in accordance with claim 1, wherein the fifth step height varies from 5 to 80% of the fourth step height.

17. Intraocular lens, in accordance with claim 1, wherein the sixth step height varies from 140 to 590% of the fifth step height.

18. Intraocular lens, in accordance with claim 1, wherein the seventh step height varies from 20 to 90% of the sixth step height.

19. Intraocular lens, in accordance with claim 1, wherein the eighth step height varies from 90 to 250% of the seventh step height.

20. Intraocular lens, in accordance with claim 1, wherein the ninth step height varies from 10 to 100% of the eighth step height.

21. Intraocular lens, in accordance with claim 1, wherein the total number (n) of steps of the diffractive profile varies from 4 to 43.

* * * * *